(12) United States Patent
Yoshimoto et al.

(10) Patent No.: US 6,723,521 B1
(45) Date of Patent: Apr. 20, 2004

(54) METHOD FOR SCREENING COMPOUNDS WHICH MODULATE GLUCOSE TRANSPORTING ACTIVITY

(76) Inventors: Makoto Yoshimoto, c/o Taisho Pharmaceutical Co., Ltd., 24-1, Takata-3-chome, Toshima-ku, Tokyo (JP); Madoka Yazaki, c/o Taisho Pharmaceutical Co., Ltd., 24-1, Takata-3-chome, Toshima-ku, Tokyo (JP); Kayo Matsumoto, c/o Taisho Pharmaceutical Co., Ltd., 24-1, Takata-3-chome, Toshima-ku, Tokyo (JP); Kiyoshi Takayama, c/o Taisho Pharmaceutical Co., Ltd., 24-1, Takata-3-chome, Toshima-ku, Tokyo (JP); Katsuki Tsuritani, c/o Taisho Pharmaceutical Co., Ltd., 24-1, Takata-3-chome, Toshima-ku, Tokyo (JP)

( * ) Notice: Subject to any disclaimer, the term of this patent is extended or adjusted under 35 U.S.C. 154(b) by 0 days.

(21) Appl. No.: 09/720,655
(22) PCT Filed: Jul. 2, 1999
(86) PCT No.: PCT/JP99/03569
§ 371 (c)(1), (2), (4) Date: Feb. 28, 2001
(87) PCT Pub. No.: WO00/01725
PCT Pub. Date: Jan. 13, 2000

(30) Foreign Application Priority Data

Jul. 2, 1998 (JP) .......................................... 10-187235

(51) Int. Cl.[7] ....................... G01N 33/53; G01N 33/567; C12P 21/06; C07K 1/00; C12N 15/74
(52) U.S. Cl. ....................... 435/7.2; 435/7.1; 435/252.3; 435/471; 435/69.1; 530/350; 536/23.5
(58) Field of Search ........................ 530/350; 536/23.5; 435/7.1, 7.2, 69.1, 471, 252.3

(56) References Cited

U.S. PATENT DOCUMENTS 6,277,565 B1 * 8/2001 Goodearl

OTHER PUBLICATIONS

Piert M, et al. J. Nucl. Med. 37(2):201–208, 1996.*
Mancini GM, et al. J. Biol. Chem. 265(21):12380–12387, 1990.*

* cited by examiner

*Primary Examiner*—Robert Landsman

(57) ABSTRACT

A gene hucep-8 coding for a novel protein HUCEP-8 having sugar-transporting activity can be obtained by cloning from a cDNA library derived from human cerebral cortex.

2 Claims, 8 Drawing Sheets

FIG. 1

Seq ID No.3 SEQUENCE-1
GATCGGGAAGACTGAGTAGGGAAGGCAGGGCTGCCNAGAAGTCTCANAGG
CACCTCACGCCAGCCATCGCGGAGAGCTCAGAGGGCCGTCCCCACCCTGC
CTCCTCCCTGCTGCTTTGCATTCACTTCCTTGGCCAGAGTCAGGGGACAG
GGAGAGAGCTCCACACTGTAACCACTGGGTCTGGGGTCCATCCTGCGCCC
AAAGACATCCACCCAGACCTCATTATTTCTTGCTCTATCATTCTGTTTCA
NTAAAGACATTTGGAATAAACGNGCATATCATAGCCTGGAAA

Seq ID No.4 SEQUENCE-2
5' TGGGCGCAGGATGGACCCCAGACCCAGTGG

Seq ID No.5 SEQUENCE-3
5' CGAACCACTGAATTCCGCATTGCAGAG

Seq ID No.6 SEQUENCE-4
5' GGCATGGCCTCGGACCCCATCTTCA

Seq ID No.7 SEQUENCE-5
5' CGCCAGGGTACTCAGAGGCCGCTC

FIG. 3

| | | | | | |
|---|---|---|---|---|---|
| Seq ID No.8 | GCGTGGCTCT | GGGCATGGCC | TCGGACCCCA | TCTTCACGCT | GGCGCCCCCG | 50 |
| | CTGCATTGCC | ACTACGGGGC | CTTCCCCCCT | AATGCCTCTG | GTTGGGAGCA | 100 |
| | GCCTCCCAAT | GCCAGCGGCG | TCAGCGTCGC | CAGCGCTGCC | CTAGCAGCCA | 150 |
| | GCGCCGCCAG | CCGTGTCGCC | ACCAGTACCG | ACCCCTCGTG | CAGCGGCTTC | 200 |
| | GCCCCGCCGG | ACTTCAACCA | TTGCCTCAAG | GATTGGGACT | ATAATGGCCT | 250 |
| | TCCTGTGCTC | ACCACCAACG | CCATCGGCCA | GTGGGATCTG | GTGTGTGACC | 300 |
| | TGGGCTGGCA | GGTGATCCTG | GAGCAGATCC | TCTTCATCTT | GGGCTTTGCC | 350 |
| | TCCGGCTACC | TGTTCCTGGG | TTACCCCGCA | GACAGATTTG | GCCGTCGCGG | 400 |
| | GATTGTGCTG | CTGACCTTGG | GGCTGGTGGG | CCCCTGTGGA | GTAGGAGGGG | 450 |
| | CTGCTGCAGG | CTCCTCCACA | GGCGTCATGG | CCCTCCGATT | CCTCTTGGGC | 500 |
| | TTTCTGCTTG | CCGGTGTTGA | CCTGGGTGTC | TACCTGATGC | GCCTGGAGCT | 550 |
| | GTGCGACCCA | ACCCAGAGGC | TTCGGGTGGC | CCTGGCAGGG | GAGTTGGTGG | 600 |
| | GGGTGGGAGG | GCACTTCCTG | TTCCTGGGCC | tGGCCCTTGT | CTCTAAGGAT | 650 |
| | TGGCGATTCC | TACAGCGAAT | GATCACCGCT | CCCTGCATCC | TCTTCCTGTT | 700 |
| | TTATGGCTGG | CCTGGTTTGT | TCCTGGAGTC | CGCACGGTGG | CTGATAGTGA | 750 |
| | AGCGGCAGAT | TGAGGAGGCT | CAGTCTGTGC | TGAGGATCCT | GGCTGAGCGA | 800 |
| | AACCGGCCCC | ATGGGCAGAT | GCTGGGGGAG | GAGGCCCAGG | AGGCCCTGCA | 850 |
| | GGACCTGGAG | AATACCTGCC | CTCTCCCTGC | AACATCCTCC | TTTTCCTTTG | 900 |
| | CTTCCCTCCT | CAACTACCGC | AACATCTGGA | AAAATCTGCT | TATCCTGGGC | 950 |
| | TTCACCAACT | TCATTGCCCA | TGCCATTCGC | CACTGCTACC | AGCCTGTGGG | 1000 |

FIG.3(CONT'D)

| | | | | | |
|---|---|---|---|---|---|
| Seq ID No.8 - cont'd | AGGAGGAGGG | AGCCCATCGG | ACTTCTACCT | GTGCTCTCTG | CTGGCCAGCG | 1050 |
| | GCACCGCAGC | CCTGGCCTGT | GTCTTCCTGG | GGGTCACCGT | GGACCGATTT | 1100 |
| | GGCCGCCGGG | GCATCCTTCT | TCTCTCCATG | ACCCTTACCG | GCATTGCTTC | 1150 |
| | CCTGGTCCTG | CTGGGCCTGT | GGGATTATCT | GAACGAGGCT | GCCATCACCA | 1200 |
| | CTTTCTCTGT | CCTTGGGCTC | TTCTCCTCCC | AAGCTGCCGC | CATCCTCAGC | 1250 |
| | ACCCTCCTTG | CTGCTGAGGT | CATCCCCACC | ACTGTCCGGG | GCCGTGGCCT | 1300 |
| | GGGCCTGATC | ATGGCTCTAG | GGGCGCTTGG | AGGACTGAGC | GGCCCGGCCC | 1350 |
| | AGCGCCTCCA | CATGGGCCAT | GGAGCCTTCC | TGCAGCACGT | GGTGCTGGCG | 1400 |
| | GCCTGCGCCC | TCCTCTGCAT | TCTCAGCATT | ATGCTGCTGC | CGGAGACCAA | 1450 |
| | GCGCAAGCTC | CTGCCCGAGG | TGCTCCGGGA | CGGGGAGCTG | TGTCGCCGGC | 1500 |
| | CTTCCCTGCT | GCGGCAGCCA | CCCCCTACCC | GCTGTGACCA | CGTCCCGCTG | 1550 |
| | CTTGCCACCC | CCAACCCTGC | CCTCTGAGCG | GCCTCTGAGT | ACCCTGGCGG | 1600 |
| | GAGGCTGGCC | CACACAGAAA | GGTGGCAAGA | AGATCGGGAA | GACTGAGTAG | 1650 |
| | GGAAGGCAGG | GCTGCCCAGA | AGTCTCAGAG | GCACCTCACG | CCAGCCATCG | 1700 |
| | CGGAGAGCTC | AGAGGGCCGT | CCCCACCCTG | CCTCCTCCCT | GCTGCTTTGC | 1750 |
| | ATTCACTTCC | TTGGCCAGAG | TCAGGGGACA | GGGAGAGAGC | TCCACACTGT | 1800 |
| | AA<u>CCACTGGG | TCTGGGGTCC | ATCCTGCGCC | CAA</u> | | |

| 1–3 | COS CELLS HAVING A VECTOR INTRODUCED THEREINTO |
|---|---|
| 1 | SUPERNATANT OBTAINED BY ULTRASONIC DISRUPTION |
| 2 | CYTOPLASM FRACTION |
| 3 | MEMBRANE FRACTION |

| 4–6 | COS CELLS HAVING pREhucep8 INTRODUCED THEREINTO |
|---|---|
| 4 | SUPERNATANT OBTAINED BY ULTRASONIC DISRUPTION |
| 5 | CYTOPLASM FRACTION |
| 6 | MEMBRANE FRACTION |

# METHOD FOR SCREENING COMPOUNDS WHICH MODULATE GLUCOSE TRANSPORTING ACTIVITY

CROSS-REFERENCE TO RELATED APPLICATIONS

This application is a National Phase Application (35 USC 371) of PCT/JP99/03569, filed Jul. 2, 1999, and claims priority of Japanese Application No. 10-187235, filed Jul. 2, 1998.

TECHNICAL FIELD

The present invention relates to a protein having sugar-transporting activity and a DNA coding for said protein.

BACKGROUND ART

Glucose, a main energy source in cranial nerve tissue has a low molecular weight of 180 but cannot pass through cell membrane rapidly because it is a polar molecule. Therefore, glucose is incorporated into cells through glucose transporters, sugar-transporting proteins that are specifically present in the form of cell membrane.

At present, as the glucose transporters, there are known those of two types, i.e., energy-dependent $Na^+$/glucose symport type for active transport of glucose against glucose concentration gradient, and facilitated diffusion transport type for transport dependent only on the difference between intracellular and extracellular glucose concentrations. It is considered that the facilitated diffusion transport type performs the principal role in cranial nerve tissue, and there have been reported GLUT1 which is present in hemoendothelial cells and participates in sugar transport in blood-brain barrier (J. Biol. Chem., 263, 15245 (1988)) and GLUT3 which is considered to transport glucose passed through blood-brain barrier, to nerve cells (J. Biol. Chem., 265, 18035 (1990)).

There are, for example, the following reports indicating the relation between neuropathy and the functional and expression abnormalities of glucose transporters: the partial deficiency of GLUT1 causes convulsion and psychogenetic retardation (N. Engl. J. Med., 325, 703 (1991)); the possibility of the functional abnormality of GLUT3 is suggested in the case of Parkinson's disease (Ann. Neurol., 32, S88 (1992)); and the expression of GLUT3 is markedly accelerated in a blood vessel in tumor (Cancer Res., 52, 3972 (1992)).

DISCLOSURE OF THE INVENTION

The present inventors earnestly investigated proteins coded for by genes that had been expressed specifically in human brain tissue, and consequently succeeded in isolating a novel protein (hereinafter referred to as HUCEP-8) and a gene coding for this protein (hereinafter referred to as hucep-8). The present inventors found that this HUCEP-8 transports monosaccharides such as glucose into cells, whereby the present invention has been accomplished.

That is, the present invention provides (1) (a) a novel protein HUCEP-8 having the amino acid sequence shown as SEQ ID NO: 1, or (b) a protein having an amino acid sequence formed by deletion, substitution or addition of one or more amino acids in the amino acid sequence shown as SEQ ID NO: 1, and having sugar-transporting activity; (2) a gene coding for either of the proteins described in (1); (3) (c) a DNA having the base sequence shown as SEQ ID NO: 2, or (d) a DNA which hybridizes with the DNA of SEQ ID NO: 2 under stringent conditions and codes for a protein having sugar-transporting activity; (4) a method for screening compounds capable of enhancing or inhibiting sugar-transporting activity, characterized by using the protein described in (1); (5) a method for screening compounds capable of enhancing or inhibiting sugar-transporting activity, characterized by using the gene described in (2) or (3); (6) a method for screening compounds capable of accelerating or inhibiting the transcription of the gene described in (2) or (3); (7) a method for screening compounds capable of accelerating or inhibiting the translocation of either of the protein described in (1); (8) a compound or a salt thereof, which is obtained by conducting the screening method described in (4), (5), (6) or (7); and (9) an antibody against the protein described in (1).

BRIEF DESCRIPTION OF DRAWINGS

In FIG. 1, sequence-1 (SEQ ID NO: 3) represents a DNA fragment having a high frequency of occurrence among recombinants obtained from a cerebral cortex cDNA library, and each of sequences-2 to -5 (SEQ ID NOS 4–7, respectively in order of appearance) represents an oligonucleotide used for cloning of DNA fragments involving sequence-1.

FIG. 3 shows the base sequence (SEQ ID NO: 8) of a DNA fragment containing the gene hucep-8.

BEST MODE FOR CARRYING OUT THE INVENTION

Figure 2:
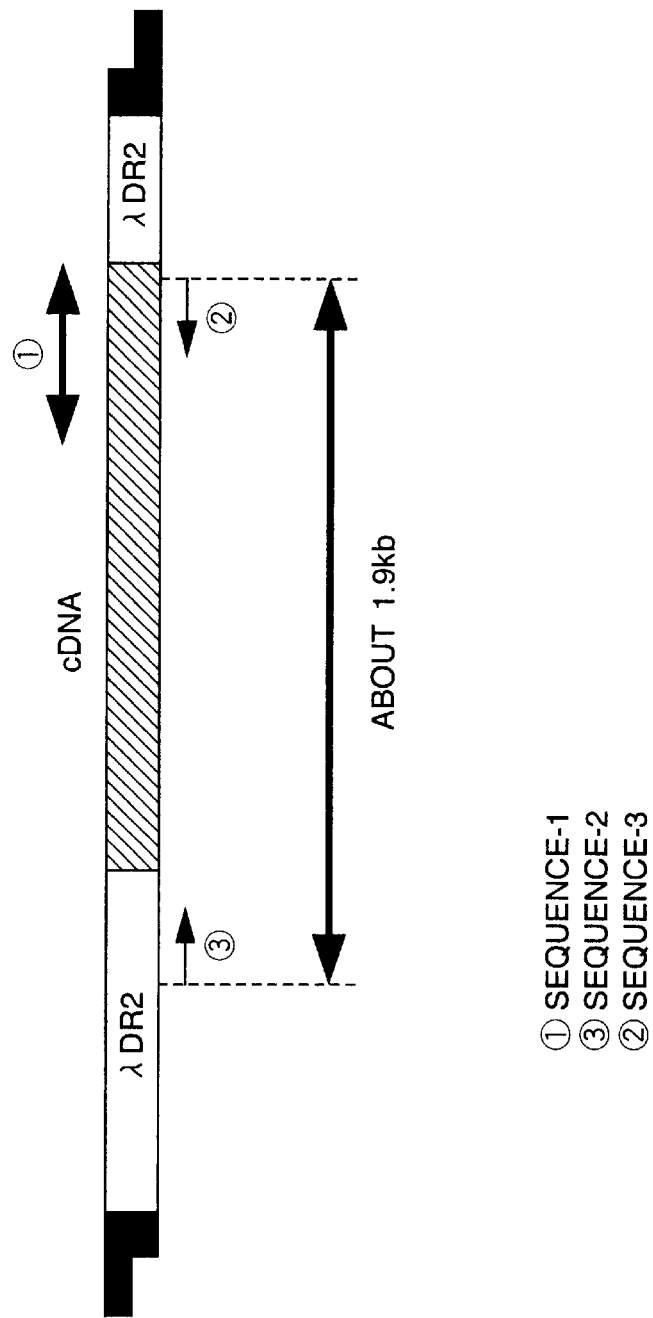
FIG. 2 shows a DNA fragment involving sequence-1.

The gene hucep-8 can be isolated as a cDNA fragments containing said gene, from a cDNA library derived from human cerebral cortex. The cDNA library used by the present inventors is that prepared by the use of human cerebral cortex mRNA which is commercially available from Clontech, though cDNAs can be similarly prepared also by using human cerebral cortex mRNA commercially available from Stratagene.

As a method for distinguishing a cDNA which is considered to have a gene expressible specifically in human brain tissue, in the above-mentioned cDNA library, there can be adopted a method of analyzing the frequency of gene expression according to the method of Okubo et al. (Okubo et al., Nature Genet., 2, 173 (1992). Specifically, cDNA is synthesized by using human cerebral cortex mRNA as a template and a primer obtained by bonding an oligo(dT) to one end of a vector plasmid subjected to circle opening by the use of suitable restriction enzymes, and then is cleaved with restriction enzymes MboI and BamHI. Since said vector is that prepared by using dam methylase-positive *Escherichia coli* as a host, the A residue of "GATC" the recognition sequence for MboI of the vector has been methylated. Therefore, MboI cleaves only a newly synthesized cDNA portion. Since said vector has only one BamHI cleavage site near the end other than the end to which the oligo(dT) has been bonded, this enzyme cleaves said vector at the one site. If a BamHI recognition sequence is present in a newly synthesized cDNA portion, cleavage by the enzyme occurs also at this site. Since BamHI and MboI give the same cohesive ends having a base sequence "GATC", the plasmid can be subjected to circle closing by treatment with DNA ligase after the cleavage with the two enzymes.

In a method adopted in the present invention, a cDNA library was constructed by transforming *Escherichia coli* by the use of the thus prepared plasmids. Therefore, this library contains a region of each mRNA extending from a poly(A) site at the 3'-end to a site at which a base sequence GATC appears for the first time on the 5'-side. A suitable number of recombinants are selected at random from said cDNA library, and cDNA is extracted from each recombinant and the whole of its base sequence is determined. Said method makes it possible to distinguish an organ-specific gene and a high-expression-frequency gene from other genes by counting cDNA fragments having a specific base sequence determined in the manner described above, which are confirmed in the recombinants selected at random. In said method, both the cDNA extraction from the recombinants and the cDNA base sequence determination can be carried out by any of various methods well known to those skilled in the art (methods described, for example, in Molecular Cloning, 2nd. ed., Cold Spring Harbor Lb. Press, 1989, and other manuals introducing standard methods for those skilled in the art; hereinafter referred to conventional methods).

In a method for distinguishing a high-expression-frequency gene, the total number of the recombinants selected at random is suitably tens to thousands, though a larger number of recombinants may be treated if necessary. The present inventors determined the all of the sequences of cDNA fragments in 770 recombinants by practicing the above-mentioned method, and selected, from these cDNA fragments, cDNA fragments having a frequency of occurrence as a cDNA having the same base sequence of 2/770 or more, as candidates for DNA fragments having a gene which is specifically expressed in human brain.

As described above, each of the above-mentioned cDNA fragments contains only a portion of the 3'-end region of mRNA. Therefore, the present inventors obtained full-length cDNAs, on the basis of information on the base sequence of said region (hereinafter 3' fragment).

The full-length cDNAs were obtained by adopting the PCR method by using a human cerebral cortex cDNA library commercially available from Clontech as a template, and using as primers a synthesized oligonucleotide with a suitable length having a base sequence in the aforesaid 3' fragment and a synthesized oligonucleotide with substantially the same length having a sequence in a vector. As a result, DNA fragments of about 1.9 kb could be amplified. In this case, a human cerebral cortex cDNA library commercially available from Stratagene can also be used as a template. The amplification can be carried out also by means of a 5' RACE kit of Clontech or Gibco by using human cerebral cortex mRNA commercially available from Clontech or Stratagene as a template. In addition, the amplification can be carried out also by screening the above-mentioned human cerebral cortex cDNA library by colony hybridization or plaque hybridization according to a conventional method by using the above-mentioned 3' fragment.

Each of the cDNA fragments amplified by the above method was inserted in pT7Blue T-vector available from Novagen, and the whole base sequences of the cDNA fragments were determined by a conventional method. In this case, two recombinant DNA clones were independently obtained for each cDNA fragment and the base sequence of the cDNA fragment was determined, whereby the base sequence was confirmed.

The specific expression in brain tissue of a gene which is considered to be present in any of the cDNA fragments selected by the above-mentioned method can be confirmed by confirming the frequency of organ-specific occurrence of said cDNA sequence by Northern hybridization. Specifically, each of mRNAs extracted from various human organs and commercially available from Clontech or Stratagene was fractionated by agarose gel electrophoresis and transferred to a membrane filter, and then hybridization was carried out by a conventional method by using as probes the cDNA fragments selected by the above-mentioned method. The present inventors investigated the organ specificity of the occurrence of said cDNA base sequence. As a result, although the occurrence of said cDNA base sequence was observed to a certain extent also in other organs and cells than brain, it was confirmed that the occurrence of said cDNA base sequence in cerebral cortex is specific as compared with that in the other organs and cells.

This fact strongly suggests the presence, in said cDNA base sequence, of a desirable gene that is expressed specifically in human brain and is indispensable for the maintenance of normal brain function.

The presence of a region coding for a protein (ORF, open reading frame) in a base sequence can be confirmed by a generally used method comprising analyzing the base sequence by the use of a computer program. In the confidence that the desired gene is present in said cDNA base sequence, the present inventors found ORF in said base sequence by utilizing a computer, and named this gene "gene hucep-8 " (an abbreviation for human cerebral protein) and a protein coded for by said gene "HUCEP-8 ".

The gene hucep-8 comprises the 1560 base pairs (bp) shown in SEQ ID NO: 2. Using this gene hucep-8, a recombinant gene can be prepared by a conventional genetic recombination technique using a suitable host-vector system. As a suitable vector, there can be used, for example, plasmids derived from *Escherichia coli* (e.g. pBR322, pUC118, etc.), plasmids derived from Bacillus subtilis (e.g. pUB110, pC194, etc.), plasmids derived from yeast (e.g. pSH19, etc.), bacteriophages and animal viruses (e.g. retrovirus and vaccinia virus). In the recombination, a translation initiation codon and a translation termination codon can be added by using suitable synthetic DNA adaptors. In addition, a suitable expression promoter is connected upstream to said gene in order to express the gene. The promoter used may be properly chosen depending on the host. For example, when the host is *Escherichia coli*, T7 promoter, lac promoter, trp promoter, λPL promoter and the like can be used. When the host is bacteria belonging to the genus Bacillus, SPO type promoters and the like can be used. When the host is yeast, PHO5 promoter, GAP promoter ADH promoter and the like can be used. When the host is animal cells, promoters derived from SV40, retrovirus promoter and the like can be used.

Said gene can be expressed as a fusion protein with another protein (e.g. glutathione S transferase, protein A or the like). The fused HUCEP-8 thus obtained by the expression can be excised by using suitable proteases (e.g. thrombin, enterokinase, etc.).

As a host utilizable for obtaining HUCEP-8 by the expression, there can be utilized various strains of *Escherichia coli*, a bacterium belonging to the genus Escherichia, various strains of *Bacillus subtilis*, a bacterium belonging to the genus Bacillus, yeasts such as various strains of *Saccharomyces cerevisiae*, and animal cells such as COS-7 cells, CHO cells, etc.

As a method for transforming host cells by using the above-mentioned recombinant vector, there can be adopted a conventional method or a method conventionally adopted in the case of cells of each host.

In addition, the present inventors recombined the gene hucep-8 by using a pREP10 (available from Invitrogen) as an expression vector, to prepare pREhucep8, a vector for expressing said gene as HUCEP-8 in cultured animal cells. Using this pREhucep8, CHO cells were transformed by the use of LIPOFECTAMINE reagent of Gibco to prepare a transformant CHO/pREhucep8. The transformed cells can be isolated by distinction by the presence of a selective marker present in the vector used or a suitable marker given or deleted. In the case of the transformation of CHO cells with pREhucep8 carried out by the present inventors, the transformant can be distinguished and isolated by employing resistance to an antibiotic hygromycin B as an indication.

The expression of the desired gene in the transformed cells obtained by the above procedure can be confirmed by Northern hybridization as described hereinafter in Examples. In COS cells transformed by pREhucep8, glucose uptake was increased as compared with COS cells having pREP10 introduced thereinto. Furthermore, it was confirmed that in SK-N-SH cells, human neuroblastoma cultured cells, the extent of the expression of hucep-8 was diminished owing to cell death.

The novel protein HUCEP-8 of the present invention is a protein with a molecular weight of 55657 daltons comprising 520 amino acid residues in all as shown as SEQ ID NO: 1. It was found that Leu Gly Tyr Pro Ala Asp Arg Phe Gly Arg Arg Gly Ile Val Leu Leu Thr (Residues 118–134 of SEQ ID NO: 1) present as the 118th residue to the 134th residue on the amino acid sequence and Leu Gly Val Thr Val Asp Arg Phe Gly Arg Arg Gly Ile Leu Leu Leu Ser (Residues 355–371 of SEQ ID NO: 1) present as the 355th residue to the 371st residue on the amino acid sequence are amino acid sequence motifs typically present in the GLUT family (Nature. 325: 641.

The present invention includes not only the DNA base sequence shown as SEQ ID NO: 2 but also a DNA that hybridizes with said DNA and codes for a physiologically active protein having sugar-transporting activity.

That is, the present invention includes the following DNA variants irrespective of their difference from the DNA base sequence shown as SEQ ID NO: 2 so long as the DNA variants hybridize with the gene hucep-8 under stringent conditions and code for a physiologically active protein having sugar-transporting activity: DNA variants obtained by a partial DNA base sequence change caused in the full-length base sequence of the gene hucep-8 by various artificial treatments such as site-specific mutation introduction, random mutatagenesis by mutagen treatment, and mutation, deletion or ligation of a DNA fragment by cleavage with restriction enzymes.

There is a possibility that a gene having a base sequence slightly different from the DNA base sequence shown as SEQ ID NO: 2 may be present on a human chromosome, independent of the gene hucep-8. Such a gene is also included in the present invention like the above-mentioned artificial variants so long as a protein coded for by this gene is a physiologically active protein having sugar-transporting activity.

The degree of the above-mentioned DNA mutation is permissible so long as the resulting variant has 90% or more homology with the DNA base sequence of the gene hucep-8. The degree of hybridization with the gene hucep-8 may be such that the hybridization with the gene hucep-8 is possible as Southern hybridization carried out under conventional conditions, for example, the following conditions: when a probe is labeled by the use of DIG DNA Labeling kit (Cat No. 1175033, available from Boehringer-Mannheim), the hybridization is carried out in Dig Easy Hyb solution (Cat No. 1603558, available from Boehringer-Mannheim) at 32° C., and a membrane is washed in a 0.5×SSC solution (containing 0.1% [w/v] SDS) at 50° C. (1×SSC solution is a buffer solution containing 0.15 M NaCl and 0.015 M sodium citrate).

The present invention also includes physiologically active proteins which are coded for by a mutant gene having a high homology with the gene hucep-8 as described above and have sugar-transporting activity.

That is, the present invention includes variants having an amino acid sequence formed by deletion, substitution or addition of one or more amino acids in the amino acid sequence of the novel protein HUCEP-8, so long as the variants are proteins having sugar-transporting activity.

The side chains of amino acids constituting a protein are different in hydrophobicity, electric charge, size and the like. Several relations capable of permitting satisfactory retention of the three-dimensional structure (also called stereostructure) of the whole protein in a sense that the relations have substantially no influence on the three-dimensional structure, have been known by experience or physicochemical measurement. For example, as to the replacement of amino acid residues, there are mentioned the following combinations: glycine (Gly) and proline (Pro); Gly and alanine (Ala) or valine (Val); leucine (Leu) and isoleucine (Ile); glutamic acid (Glu) and glutamine (Gln); aspartic acid (Asp) and asparagines (Asn); cysteine (Cys) and threonine (Thr); Thr and serine (Ser) or Ala; lysine (Lys) and arginine (Arg); etc.

Therefore, it can be said that the present invention includes variant proteins having an amino acid sequence formed by substitution, insertion, deletion or the like in the amino acid sequence shown as SEQ ID NO: 1 of the novel protein HUCEP-8, so long as the variation permits satisfactory retention of the three-dimensional structure of HUCEP-8 protein and the variant protein has sugar-transporting activity like HUCEP-8. The degree of the variation is permissible so long as the resulting variant has 90% or more homology with the amino acid sequence shown as SEQ ID NO: 1.

The present invention also provides a method for screening compounds or salts thereof, which enhance or inhibit sugar-transporting activity of the protein of the present invention, said method being characterized by using the protein of the present invention HUCEP-8. Specifically, said method is a method for screening sugar-transporting activity enhancers and sugar-transporting activity inhibitors by comparing sugar-transporting activity attained when a test compound is brought into contact with cells containing human sugar-transporting protein HUCEP-8 or their cell membrane fraction, with that attained when the contact is not made.

Any substrate may be used so long as it can serve as a substrate for the protein of the present invention. It is usually preferable to use, for example, glucose labeled with a radioisotope (e.g. $^{14}C$). The test compound includes, for example, peptides, proteins, non-peptide compounds, synthetic compounds and fermentation products. Such compounds may be novel compounds or well-known compounds. The sugar-transporting activity of the protein of the present invention, or the like can be measured according to a well-known method such as the method of Frost et al. (J. Biol. Chem., 260, 2646 (1985)).

The compound or salt thereof obtained by using the above-mentioned screening method of the present invention is a compound or a salt thereof, which is selected from the above-mentioned test compounds by screening, and the compound or salt thereof may be a novel compound or a well-known compound. For example, when the sugar-transporting activity is enhanced by about 30% or more, preferably 50% or more, as compared with that attained when the contact with a test compound is not made, this test compound can be selected as a substance capable of enhancing the sugar-transporting activity of the protein of the present invention. On the other hand, when the sugar-transporting activity is inhibited by about 30% or more, preferably 50% or more, as compared with that attained when the contact with a test compound is not made, this test compound can be selected as a substance capable of inhibiting the sugar-transporting activity of the protein of the present invention.

INDUSTRIAL APPLICABILITY

From the fact that HUCEP-8 has sugar-transporting activity, it is conjectured that the abnormal expression of the gene hucep-8 or the malfunction of HUCEP-8 is a serious obstacle to the maintenance of the function of cranial nerve.

Therefore, HUCEP-8 can be utilized for developing, for example, a compound capable of enhancing or inhibiting the sugar-transporting activity, and such a compound can be expected to be a novel therapeutic agent for cranial nerve diseases.

The present invention is explained below in detail with reference to examples but is, of course, not limited by the examples.

EXAMPLE 1

Cloning of the Gene hucep-8

1) Determination of the Partial Base Sequence of a Gene Indispensable for Maintaining the Normal Function of Cerebrum A cerebral cortex cDNA library was prepared by the method of Okubo et al. (Okubo et al. Nature Genet., 2, 173 (1992)) by using human cerebral cortex mRNA (Clontech) as a template.

Then, 770 recombinants were selected at random from said library, after which the recombinant DNAs were extracted according to a conventional method (Molecular Cloning, 2nd. ed., Cold Spring Harbor Lab. Press, 1989, hereinafter the same applied) and the base sequence on the 3'-side of the cDNA portion of each recombinant DNA was determined. For the sequencing, a DNA sequencer (ABI PRISM377) manufactured by PE Applied Biosystems and a reaction kit available from this company were used.

The frequency of occurrence of the DNA fragment in each of the 770 recombinants was analyzed to find that the frequency of occurrence of a gene having the base sequence (base sequence-1) shown in FIG. 1 was 2/770.

2) Amplification of a cDNA Fragment Containing Base Sequence-1

A cDNA fragment containing base sequence-1 was amplified by the method described below.

First, an oligonucleotide (FIG. 1; base sequence-2) having a base sequence complementary to a portion of base sequence-1 was synthesized with a DNA synthesizer (ABI380B) manufactured by PE Applied Biosystems. Then, an oligonucleotide (base sequence-3) having the same base sequence as that near the cDNA insertion site of λphage cloning vector (λDR2) was synthesized in the same manner as above. PCR was carried out by using, as a template, Human Brain cerebral cortex 5'-STRETCH cDNA library (available from Clontech Laboratories) obtained by the use of λDR2 as a cloning vector, and using the oligonucleotide having base sequence-2 and the oligonucleotide having base sequence-3, as primers. In this reaction, a kit (TAKARA LA PCR Kit Ver. 2) available from TAKARA SHUZO Co., Ltd. and PCR Thermal Cycler MP manufactured by TAKARA SHUZO Co., Ltd. were used.

| Liquid reaction composition | |
|---|---|
| cDNA library ($10^8$ pfu/ml) | 5 μl |
| 10x PCR buffer solution | 5 μl |
| 2.5 mM dNTP | 1 μl |
| 10 μM oligonucleotide (base sequence-2) | 2 μl |
| 10 μM oligonucleotide (base sequence-3) | 2 μl |
| Water | 34.5 μl |
| LA DNA polymerase | 0.5 μl |
| Total | 50 μl |

Reaction Conditions

The liquid reaction composition was maintained at 95° C. for 2 minutes, subjected to reaction at 95° C. for 20 seconds, cooled to 58° C. at a rate of −1° C./2 seconds, and maintained at 58° C. for 1 minute and then at 72° C. for 4 minutes. This cycle was repeated 35 times to amplify the desired base sequence.

DNA fragments (about 1.9 kb) having a portion of base sequence-1 were specifically amplified by the above method (FIG. 2).

3) Subcloning Into a Vector for Base Sequence Determination

The DNAs amplified in 2) were fractionated by agarose gel electrophoresis (gel concentration: 1%) according to a conventional method. The gel was stained with ethidium bromide and then irradiated with ultraviolet light, and a portion of the gel containing a desired band was cut out.

The DNA fragment was extracted from the portion of the agarose gel and purified by using Geneclean II Kit (available from Bio 101)

The purified DNA fragment was subcloned into a vector for base sequence determination, pT7 Blue T-Vector (available from Novagen) by the following method. A ligation solution was subjected to reaction at 16° C. for 1.5 hours by using a kit (TAKARA DNA Ligation Kit Ver. 2) available from TAKARA SHUZO Co., Ltd.

Using the above reaction solution, *Escherichia coli* K12 strain DH5 was transformed according to a conventional method.

The transformant was streaked on LB agar culture plate containing 50 μg/ml of ampicillin (Amp), 40 μg/ml of 5-bromo-4-chloro-3-indolyl-β-D-galactoside (X-gal) and 100 μM of isopropyl-β-D-thio-galactopyranoside (IPTG), and cultured overnight at 37° C.

The resulting white colony was inoculated into 10 ml of LB liquid medium containing 50 μg/ml of Amp, and cultured overnight at 37° C., and cells were collected by centrifugation, followed by purification of a recombinant DNA by the use of QIAprep Spin Plasmid Miniprep Kit (available from Qiagen). The recombinant DNA thus constructed was named pThucep8.

4) Determination of the Base Sequence of the DNA Fragment

Figure 4:
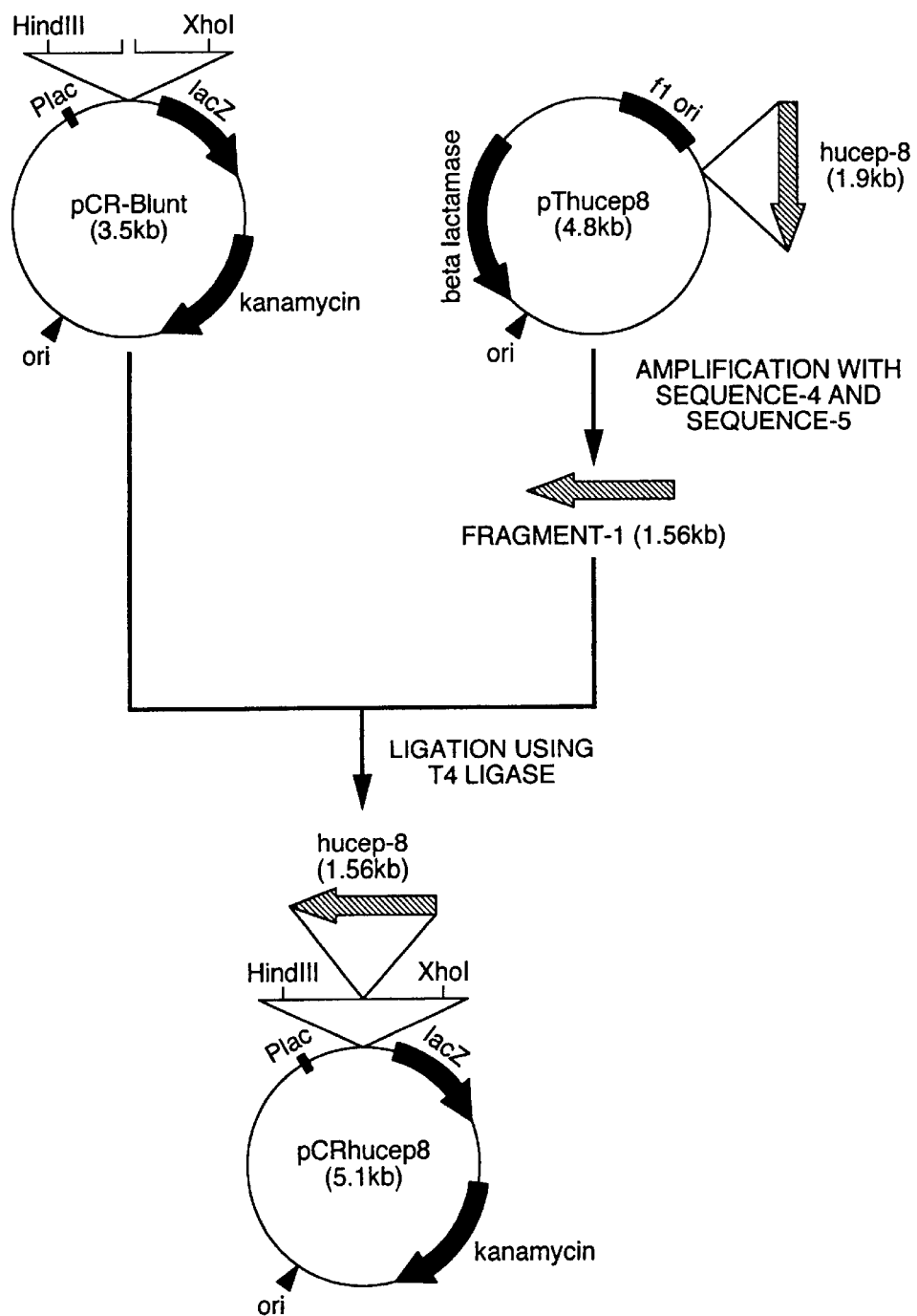
FIG. 4 shows the construction of a recombinant vector pCRhucep8.

For determining the base sequence, the di-terminator method was adopted by using a DNA sequencer manufactured by PE Applied Biosystems. On the basis of the base sequence determined, an oligonucleotide was synthesized, and the whole base sequence was determined by the primer walking method. The base sequences of both strands were determined. The whole base sequence of cDNA of said clone is shown in FIG. 3 and FIG. 4. From the fact that said base sequence contained the upstream portion of a base sequence complementary to base sequenc-2, it was confirmed that the desired gene (human cerebral protein-8, hucep-8) had been cloned.

Said cDNA contains a translation region (an open reading frame, ORF) coding for a protein (HUCEP-8) comprising 520 amino acid residues.

EXAMPLE 2

The Expression of hucep-8 Gene in CHO Cells and Analysis of its Function

1) Construction of an Expression Vector pREhucep8

Oligonucleotides having base sequence-4 and base sequence 5, respectively, were synthesized on the basis of the base sequences shown in FIG. 3 by using a DNA synthesizer (ABI 380B, mfd. by PE Applied Biosystems).

PCR was carried out under the reaction conditions described below, by using the above-mentioned recombinant DNA, pThucep8 as a template and the oligonucleotides with base sequence-4 and base sequence 5 as primers. In this reaction, Pfu DNA polymerase available from Stratagene and PCR Thermal Cycler MP manufactured by TAKARA SHUZO Co., Ltd. were used.

| Liquid reaction composition | |
|---|---|
| pThucep8 (1 μg/ml) | 1 μl |
| 10x PCR buffer solution | 5 μl |
| 2.5 mM dNTP | 8 μl |
| 10 μM oligonucleotide (base sequence-4) | 2 μl |
| 10 μM oligonucleotide (base sequence-5) | 2 μl |
| Water | 31 μl |
| Pfu DNA polymerase | 1 μl |
| Total | 50 μl |

Reaction Conditions

The liquid reaction composition was maintained at 94° C. for 1 minute, cooled to 53° C. at a rate of −1° C./2 seconds, and maintained at 53° C. for 1 minute and then at 72° C. for 3 minutes. This cycle was repeated 30 times and then the reaction solution was maintained at 72° C. for 10 minutes to amplify a desired base sequence.

The DNA fragments amplified by the above method were fractionated by agarose gel electrophoresis to purify 1.56 kb DNA fragments (fragments-1). Each fragment-1 was mixed with pcR-Blunt (available from Invitrogen), a vector previously subjected to circle opening, and ligation and transformation of Escherichia coli K12 strain DH5 were carried out under the conditions described in 3) in Example 1. Then, the transformants were cultured and their cells were collected by centrifugation, after which recombinant DNAs were purified from the cells. Of the recombinant DNAs thus constructed, a recombinant DNA having fragment-1 inserted therein so that an initiation codon for HUCEP-8 might be located on the XhoI cleavage site side of pCR-Blunt and that the termination codon might be located on the HindIII cleavage site side was named pCRhucep8 (FIG. 4).

The recombinant DNA, pCRhucep8 was cleaved with restriction enzymes HindIII and XhoI (available from TAKARA SHUZO Co., Ltd.). After the cleavage, the cleavage products were fractionated by agarose gel electrophoresis to purify a DNA fragment of about 1.6 kb (fragment-2). pREP10 (available from Invitrogen), an expression vector derived from animal cells was cleaved with restriction enzymes HindIII and XhoI (available from TAKARA SHUZO Co., Ltd.) and the resulting open circular vector (fragment-3) was purified.

Figure 5:
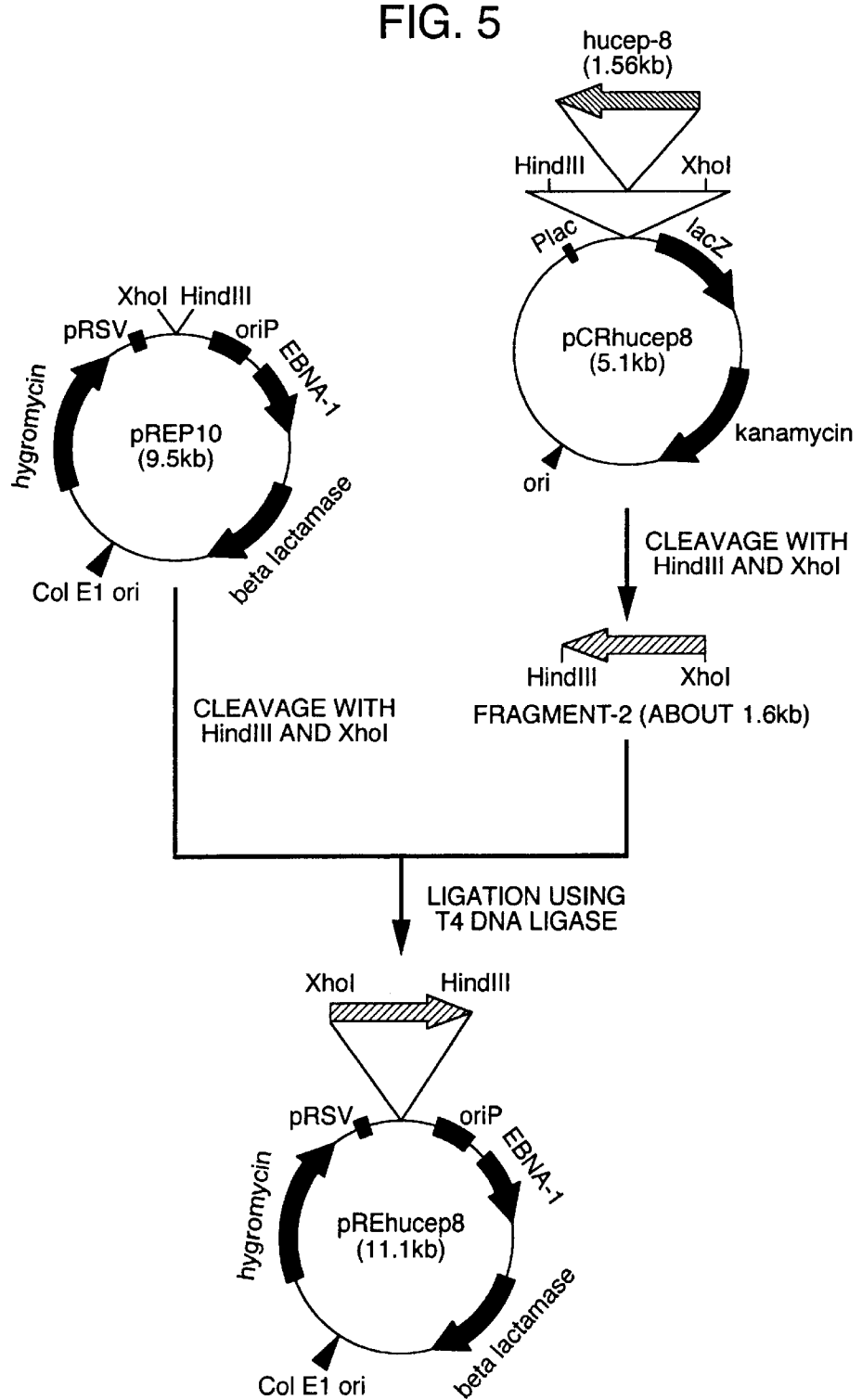
FIG. 5 shows the construction of a recombinant vector pREhucep8.

Fragment-2 and fragment 3 were mixed and ligation and transformation of Escherichia coli K12 strain DH5 were carried out under the conditions described in Example 1. Then, the transformant was cultured and its cells were collected by centrifugation, after which a recombinant DNA was purified from the cells. The recombinant DNA thus constructed was named pREhucep8 (FIG. 5).

2) Introduction Into CHO Cells and Preparation of Stable Transformants

CHO cells were cultured in a plastic Petri dish with a diameter of 60 mm. Using DMEM containing 10% of fetal bovine serum, 50 units/ml of penicillin and 50 μg/ml of streptomycin (available from Gibco; hereinafter referred to as the growth medium) as a medium, the culture was carried out at 37° C. in the presence of 5% $CO_2$.

LIPOFECTAMINE reagent (available from Gibco) was layered over cells, followed by cultivation for 3 hours. Then, the medium was replaced with the growth medium, followed by cultivation for 24 hours. After cells were dispersed in a trypsin solution, the cell suspension was divided into halves, which were poured into two Petri dishes, respectively, with a diameter of 100 mm, followed by cultivation for another 24 hour.

After the medium was removed, the growth medium containing hygromycin B (available from Calbiochem; final concentration 400 μg/ml) was used in place of the removed medium. Cultivation was carried out for 2 weeks by replacing the hygromycin B-containing grown medium with fresh medium every 3 days. At the time when colonies of cells could be visually confirmed, 5 colonies were isolated by using stainless steel cups. As reference transformants, five stable transformants were isolated after introducing only pREP10 into CHO cells in the same manner as above.

3) Confirmation of Gene Expression

Each of the isolated transformants was cultured on the grown medium containing hygromycin B (final concentration 400 μg/ml) in a plastic Petri dish with a diameter of 100 mm. At the time when the cell density corresponded to 80% confluent growth, the medium was removed, after which PBS was added and cells were recovered with a cell scraper. After the cells were precipitated by centrifugation, the supernatant was removed and mRNA was purified from the cells by using a mRNA extraction kit (available from Pharmacia Biotec). According to a conventional method, 2 μg of the mRNA was fractionated by agarose gel electrophoresis and allowed to blot a membrane (Hybond-N+, mfd. by Amersham), and Northern hybridization was carried out. As a probe, there was used a cDNA fragment corresponding to hucep-8 which had been labeled with DIG (digoxigenin). DIG oligonucleotide tailing kit (available from Boehringer-Mannheim) was used as a label, and the labeling was carried out according to the procedure described in a manual of the kit. The hybridization was carried out at 51° C. for 5 hours in a solution having the following composition (all the concentrations are final concentrations):

5×SSC

1% Blocking Buffer 0.1% Sodium N-lauroylsarcosinate 0.02% SDS

50 µg/ml polyA 1 pmol/ml DIG-labeled synthetic DNA

After completion of the hybridization, the membrane was washed at 51° C. successively with 2×SSC, 0.1% SDS, 0.5×SSC and 0.1% SDS.

After the washing, the membrane was treated by the use of a DIG luminescence detecting kit (available from Boehringer-Mannheim) according to the procedure described in a manual of the kit. For detecting signals, Hyperfilm™-ECL (available from Amersham) film was used.

As a result, it was found that the degree of expression of hucep-8 gene was higher in CHO cells having pREhucep8 introduced thereinto than in CHO cells having pREP10 introduced thereinto.

EXAMPLE 3

The Expression of hucep-8 Gene in COS Cells and Analysis of its Function

1) Introduction of pREhucep8 Into COS Cells and Preparation of Stable Transformants COS cells were cultured in a plastic Petri dish with a diameter of 60 mm. Using DMEM containing 10% of fetal bovine serum, 50 units/ml of penicillin and 50 µg/ml of streptomycin (available from Gibco; hereinafter referred to as the growth medium) as a medium, the culture was carried out at 37° C. in the presence of 5% $CO_2$.

At the time when the cell density became 50%, LIPO-FECTAMINE reagent (available from Gibco) containing pREhucep8 constructed in 1) in Example 2 was layered over cells, followed by cultivation for 24 hours. Then, the medium was replaced with the growth medium, followed by cultivation for 24 hours. After cells were dispersed in a trypsin solution, the cell suspension was divided into halves, which were poured into two Petri dishes, respectively, with a diameter of 100 mm, followed by cultivation for another 24 hour.

After the medium was removed, the growth medium containing hygromycin B (available from Calbiochem; final concentration 400 µg/ml) was used in place of the removed medium. Cultivation was carried out for 2 weeks by replacing the hygromycin B-containing grown medium with fresh medium every 3 days. At the time when colonies of cells could be visually confirmed, 5 colonies were isolated by using stainless steel cups. As reference transformants, five stable transformants were isolated after introducing only pREP10 as a vector into COS cells in the same manner as above.

2) Preparation of Anti-HUCEP-8, an Antibody Reactive Specifically With a hucep-8 Gene Product An oligopeptide corresponding to the 14 residues on the C-terminal side of a hucep-8 gene product was synthesized and then bonded to KLH by crosslinking according to a conventional method, and a rabbit was immunized with the thus obtained product. After the immunization was repeated 4 times over a period of 42 days, serum was prepared from said rabbit on the 52nd day and IgG fraction was purified by a protein A column chromatography. Then, an antibody reactive specifically with said oligopeptide was purified from said IgG fraction by an affinity column chromatography using a resin having as an immobilized oligopeptide the same oligopeptide as used as an antigen, and was named anti-HUCEP-8. All of the above operations were carried out according to a conventional method.

3) Confirmation of Gene Expression

Each of the isolated transformants was cultured on the grown medium containing hygromycin B (final concentration 400 µg/ml) in a plastic Petri dish with a diameter of 100 mm. At the time when the cell density corresponded to 80% confluent growth, the medium was removed, after which PBS was added and cells were recovered with a cell scraper. After the cells were precipitated by centrifugation, the supernatant was removed. A homogenization buffer (5 mM HEPES buffer (pH 8), 0.32 M sucrose) was added to the residue and the cells were dispersed by pipetting. The cells were disrupted with an ultrasonic cell-disrupting apparatus (mfd. by Taitec) and then non-disrupted cells were removed by centrifugation.

The supernatant (the ultrasonic lysate fraction) after the removal of the non-disrupted cells was centrifuged at 100,000×g at 4° C. for 1 hour to be fractionated into a supernatant (a cytoplasm fraction) and a precipitate. The precipitate fraction was suspended in homogenization buffer and dispersed by ultrasonication (a membrane fraction). The amount of protein in each fraction was determined by using BCA protein measuring reagent (available from Pierce).

According to a conventional method, 50 µg of protein in each fraction was fractionated by SDS-polyacrylamide gel electrophoresis and allowed to blot PVDF membrane (available from Bio-Rad). The membrane was blocked overnight at 4° C. with Blockace (available from Dai Nippon Pharmaceutical Co.) and then incubated with anti-HUCEP-8 (diluted 1,000-fold with 10% Blockace/PBS) at room temperature for 2 hours. The membrane was washed with TPBS (PBS containing 0.1% Tween 20) five times for 5 minutes each time and then incubated with ass anti-rabbit IgG having peroxidase attached thereto (available from Amersham) at room temperature for 1 hour. The thus treated membrane was washed with TPBS five times for 5 minutes each time and then treated with ECL detecting agent (available from Amersham). For detecting signals, Hyperfilm™-ECL (available from Amersham) film was used.

Figure 6:
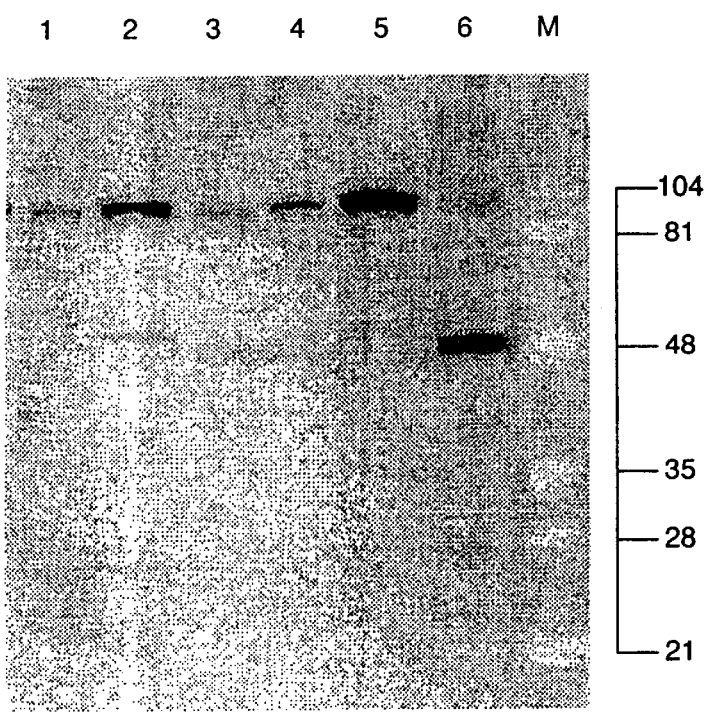
FIG. 6 shows the results of immunoblotting.

As a result, a band reactive with anti-HUCEP8 could be detected in the membrane fraction of COS cells having pREhucep8 introduced thereinto. Such a band could not be detected in the ultrasonic lysate, the cytoplasm fraction and the membrane fraction of COS cells having pREP10 introduced thereinto. The molecular weight of said band was about 50 kDa that did not agree with a molecular weight (55.7 kDa) estimated from the amino acid sequence of the hucep-8 gene product (FIG. 6). However, it is known that in general, a sugar-transporting protein has a high mobility in SDS-polyacrylamide gel electrophoresis, so that its apparent molecular weight is lower than its actual molecular weight (J. Biol. Chem., 267, 467 (1992)).

4) Confirmation of Glucose Uptake Capacity

Each of a group of COS cells having pREhucep8 introduced thereinto and a group of COS cells having pREP10 as a vector introduced thereinto were suspended in DMEM containing 2% of fetal bovine serum, 50 units/ml of penicillin and 50 µg/ml of streptomycin (available from Gibco; glucose concentration 1 g/l), seeded into 96-well CytostarT (mfd. by Amersham) at a density of $2 \times 10^4$ cells per well, and then cultured overnight at 37° C. in the presence of 5% $CO_2$. After the medium was removed, 50 µl of DMEM containing 5% BSA but not glucose and phenol red was placed in each well, followed by incubation at 37° C. for 3 hours. $^{14}$C-labeled 2-deoxyglucose (available from Daiichi Pure Chemical Co., Ltd.) was added in an amount of 0.1 μCi/50 μl/well, followed by incubation at 37° C. for 20 minutes, after which 1 mM non-radiolabeled glucose was added in an amount of 100 μl well to stop the uptake of the radiolabeled 2-deoxyglucose, and the glucose uptake capacity of cells was measured with a Micro Beta liquid scintillation counter (mfd. by Wallac).

Figure 7:
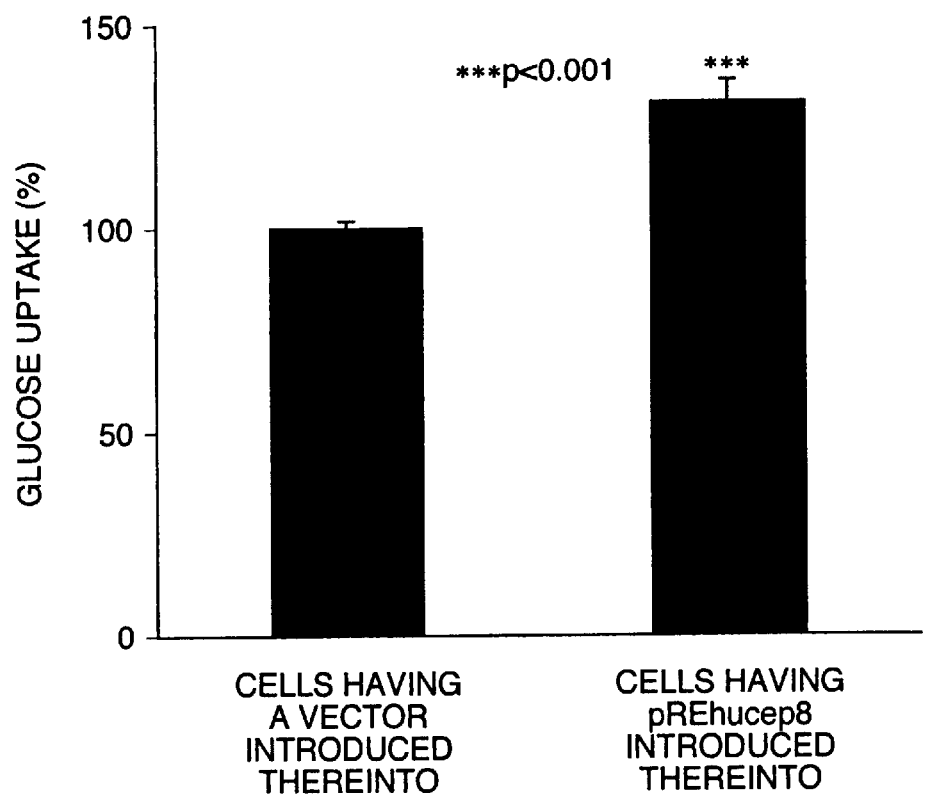
FIG. 7 shows the result of a glucose uptake test.

As a result, it was found that COS cells having pREhu-cep8 introduced thereinto had a significantly higher glucose uptake capacity than did COS cells having pREP10 as a vector introduced thereinto (FIG. 7).

What is claimed is:

1. A method for screening compounds or salts thereof capable of enhancing a glucose transporting activity, said method comprising the steps of:
   i) forming a recombinant vector comprising an isolated polynucleotide of SEQ ID NO: 2;
   ii) transforming host cells by using the recombinant vector;
   iii) bringing a test compound into contact with the transformed host cells containing a protein having the amino acid sequence of SEQ ID NO: 1 or cell membrane fraction of the transformed host cells comprising SEQ ID NO: 1, wherein said cell membrane fraction comprises the protein of SEQ ID NO: 1;
   iv) incubating the cells or the cell membrane fraction thereof from step iii in the presence of a labeled glucose;
   v) measuring the glucose uptake capacity of the incubated cells or the cell membrane fraction thereof; and
   vi) determining whether or not the glucose transporting activity is enhanced.

2. A method for screening compounds or salts thereof capable of inhibiting glucose transporting activity, said method comprising the steps of:
   i) forming a recombinant vector comprising an isolated polynucleotide of SEQ ID NO: 2;
   ii) transforming host cells by using the recombinant vector;
   iii) bringing a test compound into contact with the transformed host cells containing a protein having the amino acid sequence of SEQ ID NO: 1 or cell membrane fraction of the transformed host cells comprising SEQ ID NO: 1, wherein said cell membrane fraction comprises the protein of SEQ ID NO: 1;
   iv) incubating the cells or the cell membrane fraction thereof from step iii in the presence of a labeled glucose;
   v) measuring the glucose uptake capacity of the incubated cells or the cell membrane fraction thereof; and
   vi) determining whether or not the glucose transporting activity is inhibited.

* * * * *

UNITED STATES PATENT AND TRADEMARK OFFICE
CERTIFICATE OF CORRECTION

PATENT NO. : 6,723,521 B1
DATED : April 20, 2004
INVENTOR(S) : Yoshimoto et al.

It is certified that error appears in the above-identified patent and that said Letters Patent is hereby corrected as shown below:

Title page,
Item [73], Assignee, should read as follows:
-- [73]   Assignee:   Taisho Pharmaceutical Co., Ltd., JP --.

Column 5,
Line 38, "641." should read -- 641) --.

Column 13,
Line 6, "100 µl well" should read -- 100 µl/well --.

Column 21,
Line 24, delete "a".

Signed and Sealed this

Fifth Day of April, 2005

JON W. DUDAS
*Director of the United States Patent and Trademark Office*

SEQUENCE LISTING

<160> NUMBER OF SEQ ID NOS: 8

<210> SEQ ID NO 1
<211> LENGTH: 519
<212> TYPE: PRT
<213> ORGANISM: Homo sapiens

<400> SEQUENCE: 1

Met Ala Ser Asp Pro Ile Phe Thr Leu Ala Pro Pro Leu His Cys His
 1               5                  10                  15

Tyr Gly Ala Phe Pro Pro Asn Ala Ser Gly Trp Glu Gln Pro Pro Asn
            20                  25                  30

Ala Ser Gly Val Ser Val Ala Ser Ala Leu Ala Ala Ser Ala Ala
        35                  40                  45

Ser Arg Val Ala Thr Ser Thr Asp Pro Ser Cys Ser Gly Phe Ala Pro
    50                  55                  60

Pro Asp Phe Asn His Cys Leu Lys Asp Trp Asp Tyr Asn Gly Leu Pro
65                  70                  75                  80

Val Leu Thr Thr Asn Ala Ile Gly Gln Trp Asp Leu Val Cys Asp Leu
                85                  90                  95

Gly Trp Gln Val Ile Leu Glu Gln Ile Leu Phe Ile Leu Gly Phe Ala
            100                 105                 110

Ser Gly Tyr Leu Phe Leu Gly Tyr Pro Ala Asp Arg Phe Gly Arg Arg
        115                 120                 125

Gly Ile Val Leu Leu Thr Leu Gly Leu Val Gly Pro Cys Gly Val Gly
    130                 135                 140

Gly Ala Ala Ala Gly Ser Ser Thr Gly Val Met Ala Leu Arg Phe Leu
145                 150                 155                 160

Leu Gly Phe Leu Leu Ala Gly Val Asp Leu Gly Val Tyr Leu Met Arg
                165                 170                 175

Leu Glu Leu Cys Asp Pro Thr Gln Arg Leu Arg Val Ala Leu Ala Gly
            180                 185                 190

Glu Leu Val Gly Val Gly Gly His Phe Leu Phe Leu Gly Leu Ala Leu
        195                 200                 205

Val Ser Lys Asp Trp Arg Phe Leu Gln Arg Met Ile Thr Ala Pro Cys
    210                 215                 220

Ile Leu Phe Leu Phe Tyr Gly Trp Pro Gly Leu Phe Leu Glu Ser Ala
225                 230                 235                 240

Arg Trp Leu Ile Val Lys Arg Gln Ile Glu Glu Ala Gln Ser Val Leu
                245                 250                 255

Arg Ile Leu Ala Glu Arg Asn Arg Pro His Gly Gln Met Leu Gly Glu
            260                 265                 270

Glu Ala Gln Glu Ala Leu Gln Asp Leu Glu Asn Thr Cys Pro Leu Pro
        275                 280                 285

Ala Thr Ser Ser Phe Ser Phe Ala Ser Leu Leu Asn Tyr Arg Asn Ile
    290                 295                 300

-continued

```
Trp Lys Asn Leu Leu Ile Leu Gly Phe Thr Asn Phe Ile Ala His Ala
305                 310                 315                 320

Ile Arg His Cys Tyr Gln Pro Val Gly Gly Gly Ser Pro Ser Asp
            325                 330                 335

Phe Tyr Leu Cys Ser Leu Leu Ala Ser Gly Thr Ala Ala Leu Ala Cys
            340                 345                 350

Val Phe Leu Gly Val Thr Val Asp Arg Phe Gly Arg Gly Ile Leu
            355                 360                 365

Leu Leu Ser Met Thr Leu Thr Gly Ile Ala Ser Leu Val Leu Leu Gly
            370                 375                 380

Leu Trp Asp Tyr Leu Asn Glu Ala Ala Ile Thr Thr Phe Ser Val Leu
385                 390                 395                 400

Gly Leu Phe Ser Ser Gln Ala Ala Ala Ile Leu Ser Thr Leu Leu Ala
            405                 410                 415

Ala Glu Val Ile Pro Thr Thr Val Arg Gly Arg Gly Leu Gly Leu Ile
            420                 425                 430

Met Ala Leu Gly Ala Leu Gly Gly Leu Ser Gly Pro Ala Gln Arg Leu
            435                 440                 445

His Met Gly His Gly Ala Phe Leu Gln His Val Val Leu Ala Ala Cys
            450                 455                 460

Ala Leu Leu Cys Ile Leu Ser Ile Met Leu Leu Pro Glu Thr Lys Arg
465                 470                 475                 480

Lys Leu Leu Pro Glu Val Leu Arg Asp Gly Glu Leu Cys Arg Arg Pro
            485                 490                 495

Ser Leu Leu Arg Gln Pro Pro Thr Arg Cys Asp His Val Pro Leu
            500                 505                 510

Ala Thr Pro Asn Pro Ala Leu
            515
```

<210> SEQ ID NO 2
<211> LENGTH: 1560
<212> TYPE: DNA
<213> ORGANISM: Homo sapiens

<400> SEQUENCE: 2

```
atggcctcgg accccatctt cacgctggcg ccccgctgc attgccacta cggggccttc      60
cccctaatg cctctggttg ggagcagcct cccaatgcca gcggcgtcag cgtcgccagc     120
gctgccctag cagccagcgc cgccagccgt gtcgccacca gtaccgaccc ctcgtgcagc     180
ggcttcgccc cgccggactt caaccattgc ctcaaggatt gggactataa tggccttcct     240
gtgctcacca ccaacgccat cggccagtgg gatctggtgt gtgacctggg ctggcaggtg     300
atcctggagc agatcctctt catcttgggc tttgcctccg gctacctgtt cctgggttac     360
cccgcagaca gatttggccg tcgcgggatt gtgctgctga ccttgggggct ggtgggcccc     420
tgtggagtag gaggggctgc tgcaggctcc tccacaggcg tcatggcct ccgattcctc     480
ttgggctttc tgcttgccgg tgttgacctg ggtgtctacc tgatgcgcct ggagctgtgc     540
gacccaaccc agaggcttcg ggtggccctg caggggagt tggtggggggt gggagggcac     600
ttcctgttcc tgggcctggc ccttgtctct aaggattggc gattcctaca gcgaatgatc     660
accgctccct gcatcctctt cctgttttat ggctggcctg gtttgttcct ggagtccgca     720
cggtggctga tagtgaagcg gcagattgag gaggctcagt ctgtgctgag gatcctggct     780
gagcgaaacc ggccccatgg gcagatgctg ggggaggagg cccaggaggc cctgcaggac     840
ctggagaata cctgccctct ccctgcaaca tcctcctttt cctttgcttc cctcctcaac     900
```

-continued

```
taccgcaaca tctggaaaaa tctgcttatc ctgggcttca ccaacttcat tgcccatgcc      960
attcgccact gctaccagcc tgtgggagga ggagggagcc catcggactt ctacctgtgc     1020
tctctgctgg ccagcggcac cgcagccctg gcctgtgtct tcctgggggt caccgtggac     1080
cgatttggcc gccggggcat ccttcttctc tccatgaccc ttaccggcat tgcttccctg     1140
gtcctgctgg gcctgtggga ttatctgaac gaggctgcca tcaccacttt ctctgtcctt     1200
gggctcttct cctcccaagc tgccgccatc ctcagcaccc tccttgctgc tgaggtcatc     1260
cccaccactg tccggggccg tggcctgggc ctgatcatgg ctctagggc gcttggagga      1320 ctgagcggcc cggccagcg cctccacatg ggccatggag ccttcctgca gcacgtggtg      1380
ctggcggcct cgcccctcct ctgcattctc agcattatgc tgctgccgga gaccaagcgc     1440
aagctcctgc ccgaggtgct ccgggacggg gagctgtgtc gccggccttc cctgctgcgg     1500
cagccacccc ctacccgctg tgaccacgtc ccgctgcttg ccaccccaa ccctgccctc      1560
```

<210> SEQ ID NO 3
<211> LENGTH: 292
<212> TYPE: DNA
<213> ORGANISM: Homo sapiens
<220> FEATURE:
<221> NAME/KEY: modified_base
<222> LOCATION: (36)
<223> OTHER INFORMATION: a, c, g, t, unknown or other
<220> FEATURE:
<221> NAME/KEY: modified_base
<222> LOCATION: (47)
<223> OTHER INFORMATION: a, c, g, t, unknown or other
<220> FEATURE:
<221> NAME/KEY: modified_base
<222> LOCATION: (251)
<223> OTHER INFORMATION: a, c, g, t, unknown or other
<220> FEATURE:
<221> NAME/KEY: modified_base
<222> LOCATION: (273)
<223> OTHER INFORMATION: a, c, g, t, unknown or other

<400> SEQUENCE: 3

```
gatcgggaag actgagtagg gaaggcaggg ctgccnagaa gtctcanagg cacctcacgc       60
cagccatcgc ggagagctca gagggccgtc cccaccctgc ctcctccctg ctgctttgca     120
ttcacttcct tggccagagt caggggacag ggagagagct ccacactgta accactgggt     180
ctggggtcca tcctgcgccc aaagacatcc acccagacct cattatttct tgctctatca     240
ttctgtttca ntaaagacat ttggaataaa cgngcatatc atagcctgga aa             292
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
tgggcgcagg atggacccca gacccagtgg                                        30
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 5
cgaaccactg aattccgcat tgcagag                                          27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcatggcct cggaccccat cttca                                            25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgccagggta ctcagaggcc gctc                                             24

<210> SEQ ID NO 8
<211> LENGTH: 1833
<212> TYPE: DNA
<213> ORGANISM: Homo sapiens

<400> SEQUENCE: 8
gcgtggctct gggcatggcc tcggacccca tcttcacgct ggcgcccccg ctgcattgcc      60
actacggggc cttccccct aatgcctctg gttgggagca gcctcccaat gccagcggcg     120
tcagcgtcgc cagcgctgcc ctagcagcca gcgccgccag ccgtgtcgcc accagtaccg    180
acccctcgtg cagcggcttc gccccgccgg acttcaacca ttgcctcaag gattgggact    240
ataatggcct tcctgtgctc accaccaacg ccatcggcca gtgggatctg gtgtgtgacc    300
tgggctggca ggtgatcctg gagcagatcc tcttcatctt gggctttgcc tccggctacc    360
tgttcctggg ttaccccgca gacagatttg gccgtcgcgg gattgtgctg ctgaccttgg    420
ggctggtggg ccctgtggga gtaggagggg ctgctgcagg ctcctccaca ggcgtcatgg    480
ccctccgatt cctcttgggc tttctgcttg ccggtgttga cctgggtgtc tacctgatgc    540
gcctggagct gtgcgaccca acccagaggc ttcgggtggc cctggcaggg gagttggtgg    600
gggtgggagg gcacttcctg ttcctgggcc tggcccttgt ctctaaggat tggcgattcc    660
tacagcgaat gatcaccgct ccctgcatcc tcttcctgtt ttatggctgg cctggttttgt   720 tcctggagtc cgcacggtgg ctgatagtga agcggcagat tgaggaggct cagtctgtgc    780
tgaggatcct ggctgagcga aaccggcccc atgggcagat gctggggag gaggcccagg     840 aggccctgca ggacctggag aatacctgcc ctctccctgc aacatcctcc ttttcctttg    900
cttccctcct caactaccgc aacatctgga aaatctgct tatcctgggc ttcaccaact    960
tcattgccca tgccattcgc cactgctacc agcctgtggg aggaggaggg agcccatcgg   1020
acttctacct gtgctctctg ctggccagcg gcaccgcagc cctggcctgt gtcttcctgg   1080
gggtcaccgt ggaccgattt ggccgccggg gcatccttct tctctccatg acccttaccg   1140
gcattgcttc cctggtcctg ctgggccctgt gggattatct gaacgaggct gccatcacca   1200 cttctctgt ccttgggctc ttcttcctccc aagctgccgc catcctcagc accctccttg    1260
```

-continued

```
ctgctgaggt catcccacc actgtccggg gccgtggcct gggcctgatc atggctctag    1320
gggcgcttgg aggactgagc ggcccggccc agcgcctcca catgggccat ggagccttcc    1380
tgcagcacgt ggtgctggcg gcctgcgccc tcctctgcat tctcagcatt atgctgctgc    1440
cggagaccaa gcgcaagctc ctgcccgagg tgctccggga cggggagctg tgtcgccggc    1500
cttccctgct gcggcagcca cccctaccc gctgtgacca cgtcccgctg cttgccaccc    1560
ccaaccctgc cctctgagcg gcctctgagt accctggcgg gaggctggcc cacacagaaa    1620
ggtggcaaga agatcgggaa gactgagtag ggaaggcagg gctgcccaga agtctcagag    1680
gcacctcacg ccagccatcg cggagagctc agagggccgt ccccaccctg cctcctccct    1740
gctgctttgc attcacttcc ttggccagag tcagggaca gggagagagc tccacactgt    1800
aaccactggg tctggggtcc atcctgcgcc caa                                 1833
```